United States Patent [19]
Oltean et al.

[11] Patent Number: 5,908,942
[45] Date of Patent: Jun. 1, 1999

[54] EPOXIDATION OF BUTADIENE USING CESIUM FLUORIDE PROMOTED SILVER CATALYST WITH ENHANCED THERMAL STABILITY UNDER REACTION CONDITIONS

[75] Inventors: George Leslie Oltean, Rochester, N.Y.; John Robert Monnier, Kingsport, Tenn.

[73] Assignee: Eastman Chemical Company, Kingsport, Tenn.

[21] Appl. No.: 08/703,306

[22] Filed: Aug. 26, 1996

Related U.S. Application Data

[60] Provisional application No. 60/003,845, Sep. 15, 1995.
[51] Int. Cl.$^6$ .................................................. C07D 301/10
[52] U.S. Cl. ............................................ 549/537; 549/536
[58] Field of Search ....................................... 549/536, 537

[56] References Cited

U.S. PATENT DOCUMENTS

| | | | |
|---|---|---|---|
| 4,039,561 | 8/1977 | Mitsuhata et al. | 260/348.34 |
| 4,169,009 | 9/1979 | Wagner et al. | 156/636 |
| 4,267,073 | 5/1981 | Nielsen et al. | 252/455 |
| 4,389,338 | 6/1983 | Mitsuhata et al. | 252/463 |
| 4,769,358 | 9/1988 | Kishimoto et al. | 502/348 |
| 4,897,498 | 1/1990 | Monnier et al. | 549/534 |
| 4,950,773 | 8/1990 | Monnier et al. | 549/534 |
| 4,994,588 | 2/1991 | Kapicak et al. | 549/534 |
| 5,081,096 | 1/1992 | Monnier et al. | 502/348 |
| 5,102,848 | 4/1992 | Soo et al. | 502/218 |

FOREIGN PATENT DOCUMENTS

| | | |
|---|---|---|
| 0 243 996 | 11/1987 | European Pat. Off. . |
| 0 244 895 | 11/1987 | European Pat. Off. . |
| 0 369 902 | 5/1990 | European Pat. Off. . |
| 0 425 020 A1 | 5/1991 | European Pat. Off. . |
| 0 059 422 | 9/1992 | European Pat. Off. . |
| 90/11279 | 10/1990 | WIPO . |
| 93/03024 | 2/1993 | WIPO . |

*Primary Examiner*—Bernard Dentz
*Attorney, Agent, or Firm*—Cheryl J. Tubach; Michael J. Blake; Harry J. Gwinnell

[57] ABSTRACT

Disclosed is a process for the selective epoxidation of olefins, including diolefins, having more than 2 carbon atoms by the catalytic oxidation of such an olefin in the presence of a supported, fluorine-promoted, silver catalyst.

6 Claims, No Drawings

EPOXIDATION OF BUTADIENE USING CESIUM FLUORIDE PROMOTED SILVER CATALYST WITH ENHANCED THERMAL STABILITY UNDER REACTION CONDITIONS

This is a continuation of Provisional Application No. 60003,845 filed Sep. 15, 1995.

TECHNICAL FIELD

This invention relates to an improved process for the production of epoxides from olefins. More particularly, this invention relates to the use of an epoxidation catalyst which improves process operability.

BACKGROUND OF THE INVENTION

A process to selectively monoepoxidize dienes is disclosed in U.S. Pat. No. 4,897,498. The diene of most commercial interest to epoxidize is butadiene. The resulting desirable product is 3,4-epoxy-1-butene (also known as butadiene monoepoxide, epoxybutene or EpB™ oxirane).

The catalysts employed in the reaction are promoted, supported silver containing catalysts. The promoters may be alkali metal halides. One example of a such catalyst is an $Al_2O_3$ supported, CsCl-promoted Ag catalyst. Under standard epoxidation conditions, the halide is being continually removed from the surface of the silver and consumed, thus causing the catalyst to become unstable and the reaction to be nonselective. In addition, the complete combustion of $C_4H_6$ to $CO_2$ and $H_2O$ occurs and the reaction becomes thermally unstable. Excessive production of $CO_2$ and $H_2O$ is undesirable because it renders temperature control in the process extremely difficult with thermal run-aways to over 400–500° C. within 8 hours of being on line and valuable feed stock is consumed. Once a thermal run-away occurs, the catalyst becomes irreversibly non-selective. The temperature in the process must be carefully controlled to avoid local over-heating of the catalyst, which results in accelerated promoter loss, greater rates of combustion and possible permanent degradation of the catalyst making it unfit for further use.

This problem is overcome, as disclosed in U.S. Pat. No. 4,950,773, by the carefully controlled addition of organic halides to the reactor feed stream soon after the reactor is brought on line. The halide of the feed stream is continually deposited in a controlled manner on the catalyst surface at a rate equal to the amount of halide being removed from the catalyst such that the catalyst is stabilized. However, this is a delicate balance to maintain. If too much organic halide is deposited the catalyst deactivates; if too little is deposited the catalyst becomes non-selective and unstable.

Thus, there exists a need in the art to have a catalyst for the monoepoxidation of dienes that reduces catalyst degradation, promotes thermal stability, provides increased selectivity, and does not require extensive monitoring. This is especially critical during the first hours and possibly days that a fresh catalyst is exposed to the butadiene plus oxygen-containing feed stream. This period of time, during which a catalyst reaches steady-state catalytic activity, is critical in defining the resultant activity and stability of promoted silver catalysts for the epoxidation of butadiene. Accordingly, it is to the provision of such an improved catalyst for the production of epoxides that the present invention is primarily directed.

SUMMARY OF THE INVENTION

A process for the preparation of a monoepoxide of an olefin selected from norbornene, norbornadiene and olefins having the general formula

wherein $R^1$ is hydrogen or alkyl and $R^2$ is an aryl group, a tertiary alkyl group or the group having the formula

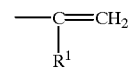

with the proviso that $R^1$ contains no hydrogen atoms in a position allylic to the ethylenic unsaturation, comprises contacting the olefin with an oxygen-containing gas in the presence of a supported, fluorine-promoted, silver catalyst at epoxide-forming conditions of pressure and temperature. The catalyst consists essentially of a catalyst support material having a surface area of less than 10 square meters per gram. On the surface of the catalyst is 0.1 to 50 weight percent silver, 10 to 5000 ppm fluorine, and an amount of cation selected from the group consisting of thallium, alkali metals and alkaline earth metals in the same weight range as the amount of fluorine.

DESCRIPTION OF THE INVENTION

The prior art problems of catalyst degradation, thermal instability and loss of selectivity in the epoxidation of non-allylic olefins are unexpectedly alleviated by using a fluorine (F) promoted silver (Ag) catalyst. It has been discovered that certain olefins may be converted to their corresponding epoxides and monoepoxides by contacting such olefins with an oxygen-containing gas in the presence of this fluorine promoted silver catalyst to provide improved operability, i.e. resistance to thermal run-away, under reaction conditions without the need to rejuvenate fluorine by the addition of organic halides to the reactor feed stream.

The interaction between fluorine and the silver catalyst is unknown but is presumed to result in the formation of some type of Ag—F species. This Ag—F moiety is believed to serve as a reaction moderator just as the presumed Ag—Cl moiety of the prior art did. However, fluorine is believed to be removed from the silver catalyst at a much slower rate since the Ag—F bond is more stable than the Ag—Cl bond. Because of this slower rate of halogen moderator loss as compared to those halogens of the prior art, the fluorine promoted silver catalyst makes control of the process easier. Wider temperature operating limits are now possible since there is greater resistance to thermal run-aways.

The type of catalysts used in the present invention are silver promoted with fluorine as an anion along with thallium, alkali metal and alkaline earth metal cations. Examples of alkali metal cations include sodium, potassium, rubidium, and cesium. Examples of alkaline earth metal cations include calcium and barium cations. Combinations of two or more of the above cations can be used in conjunction with the fluorine anion. The amount of cation is in the same weight range as the amount of fluorine anion.

The preferred catalyst is Ag promoted with CsF on $Al_2O_3$ support. By promoting the Ag catalyst or Ag salt precursor with CsF upon deposition, some interaction of the F with the $Al_2O_3$ surface, as well as with Ag and Cs, may occur. Thus, the chemical form of the fluorine component of the finished catalyst is not known.

The catalysts consist essentially of a catalyst support material having deposited on its surface 0.1 to 50 weight percent, preferably 1 to 30 weight percent, silver and 10 to 5000 parts per million (ppm) by weight fluorine. The weight percentage silver and ppm fluorine are based on the total weight of the catalyst, i.e., the finished catalyst. Although the fluorine component of the catalyst may exist as a salt, oxide or hydroxide of fluorine, the fluorine concentration of the catalyst is based on fluorine alone.

The support component of the catalysts may be selected from the large number of conventional, porous, refractory catalyst carriers or support materials which are essentially inert in the presence of the ethylenically unsaturated compound and oxygen-containing gas feeds and the products in the processes in which the catalysts are employed. Such conventional materials may be of natural or synthetic origin and preferably are of a macroporous structure, that is, a structure having a surface area below 10 $m^2$/g. These support materials typically have an apparent porosity of greater than 20%. Supports having a siliceous and/or aluminous composition are, in general, preferred. Specific examples of suitable supports are the aluminum oxides (including the materials sold under the trade name "Alundum"), pumice, magnesia, zirconia, kieselguhr, fuller's earth, silicon carbide, porous agglomerates comprising silicon and/or silicon carbide, silica, selected clays, artificial and natural zeolites and ceramics. Refractory supports particularly useful in the preparation of the catalysts useful in the process of our invention comprise the aluminous materials, in particular those containing alpha alumina. In the case of alpha alumina-containing supports, preference is given to those having a specific surface area as measured by the B.E.T. method of from 0.03 to 10 $m^2$/g and an apparent porosity as measured by conventional mercury or water absorption techniques of from 25 to 50% by volume. The B.E.T. method for determining specific surface area is described in detail in Brunauer, S., Emmett, P. H., and Teller, E., J. Am. Chem. Soc., 60, 309–16 (1938).

The following materials are specific examples of the catalyst supports which may be used.

I. Norton SN-06595, a fluidizable powder having a surface area of 0.26 $m^2$/g, a total pore volume of 0.675 cc (Hg)/gm, median pore diameter 19 microns ($\mu$), a packing density of 0.98 g/$cm^3$, and a chemical composition (weight percent) of:
$Al_2O_3$ - 84.7, $SiO_2$ - 13.4, $Fe_2O_3$ - 0.21, $TiO_2$ - 0.47, CaO - 0.21, MgO - 0.12, $Na_2O$ - 0.15, $K_2O$ - 0.26).

II. Norton SN-08228, 0.1875 inch (4.76 mm) pellets with a surface area of 0.26 $m^2$/g, a total pore volume of 0.23 cc(Hg)/gm, median pore diameter of 19 $\mu$, a packing density of 0.90 g/$cm^3$, and a chemical composition (weight percent) of: alumina - 84.7, $SiO_2$ - 13.4, $Fe_2O_3$ - 0.21, $TiO_2$ - 0.47, CaO - 0.21, MgO - 0.12, $Na_2O$ - 0.15, $K_2O$ - 0.26.

III. Norton SA-5252, 0.1875 inch (4.76 mm) spheres with a surface area of 0.39 $m^2$/g, a total pore volume of 0.36 cc(Hg)/gm, median pore diameter of 5.4 $\mu$, a packing density of 0.94 g/$cm^3$ and a chemical composition (weight percent) as follows: $Al_2O_3$ - 93.1, $SiO_2$ -5.6, $Fe_2O_3$ - 0.3, $TiO_2$ - 0.1, CaO - 0.1, MgO - 0.3, $Na_2O$ - 0.1, $K_2O$ - 0.1.

IV. Norton 5552 Alumina Rings - 0.25 inch (6.35 mm) rings having a surface area of 0.43 $m^2$/g, a total pore volume of 0.37 cc (Hg)/gm, a median pore diameter of 7 $\mu$, a packing density of 0.80 g/$cm^3$, and a chemical composition (weight percent) of: $Al_2O_3$ - 93.1, $SiO_2$ - 5.6, $Fe_2O_3$ - 0.3, $TiO_2$ - 0.1, CaO - 0.1, MgO - 0.3, $Na_2O$ - 0.1, $K_2O$ - 0.1.

V. Norton SN-82501, 0.1875 inch (4.76 mm) spheres having a surface area of 0.13 $m^2$/g, a total pore volume of 0.37 cc(Hg)/gm, a median pore diameter of 32.5 $\mu$, a packing density of 0.88 g/$cm^3$, and a chemical composition (weight percent) of: $Al_2O_3$ - 85.0, $SiO_2$ - 12.0, and the remaining 3% as $Fe_2O_3$, TiO2, CaO, MgO, $Na_2O$ and $K_2O$.

Although not preferred, other support materials which may be used include zinc oxide, e.g., having a surface area of 3.9 $m^2$/g and a particle size of 75–250 $\mu$; titania, e.g., having a surface area of 0.5 $m^2$/g and a particle size of 40–75 $\mu$; calcium oxide; silica, e.g., having a surface area of 0.18 $m^2$/g and a particle size of 75–250 $\mu$; barium oxide, e.g., having a surface area of 1 $m^2$/g and a particle size of 40–75 $\mu$; boron nitride; silicon nitride; and silicon carbide.

A preferred class of support materials comprise low surface area, fused, alpha alumina supports which have relatively uniform pore diameters and are more fully characterized by having (1) B.E.T. specific surface areas of from 0.1 $m^2$/g to 2.0 $m^2$/g, preferably 0.3 $m^2$/g, and (2) apparent porosities of from 42% to 60%, preferably from 46% to 58%.

The actual physical form of the catalyst support is not particularly important. While the form of the catalyst support has little effect on catalyst activity, practical considerations such as ease of heat transfer, mass transfer, pressure drop due to fluid flow restrictions, efficiency of gas-liquid-solid contacting, catalyst durability, and the like make the use of defined shapes such as spheres, pellets, extrudates, rings, saddles, and the like preferred. Conventional commercial fixed-bed reactors used in the epoxidation of ethylenically-unsaturated compounds typically are in the form of a plurality of parallel, or series of, elongated tubes (in a suitable shell). In such reactors, it is desirable to employ a support formed into a rounded shape, such as, for example, spheres, pellets, rings, tablets, and the like, having diameters of from 0.1 inch (2.54 mm) to 0.8 inch (20.32 mm).

The catalyst may also have additional components which may modify catalyst activity and/or selectivity. Such additives may be incorporated into the finished catalyst to aid in catalyst preparation, e.g., binders and die lubricants; as extenders to reduce the cost of catalyst preparation; to extend the operating ranges for reaction temperature and/or pressure; to increase catalyst lifetime under reaction conditions; or to modify the amounts of catalyst promoters employed to produce enhance catalyst activity.

The supported, fluorine-promoted, silver catalysts may be prepared according to known procedures such as those described in U.S. Pat. Nos. 4,039,561, 4,169,009, 4,267,073, 4,389,338, 4,769,358, and 5,081,096. Thus, a fluorine compound may be deposited prior to, simultaneous with or subsequent to the deposition of the silver compound.

Most any source of silver is suitable for use in preparing the catalyst. Preparation of supported catalysts involves impregnation of a support with a solution of a silver compound, such soluble silver compounds which are preferred include silver nitrate, silver oxalate, and silver acetate. Certain organic silver compounds require the addition of ammonia or an amine in order to solubilize the organic silver compound in an aqueous medium; thus, the use of such solvation-promoting additives is contemplated in the practice of the present invention.

The olefin reactants which may be used in the process include norbornene, norbornadiene, and olefins having the general formula

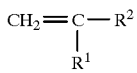   (I)

wherein $R^1$ is hydrogen or alkyl and $R^2$ is an aryl group, a tertiary alkyl group such as tertiary butyl, tertiary amyl, or tertiary octyl, or the group having the formula

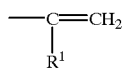

with the proviso that $R^1$ contains no hydrogen atoms in a position allylic to the ethylenic unsaturation, i.e., the >C=C<group or groups. The alkyl groups represented by $R^1$ may be unsubstituted or substituted alkyl having up to 12 carbon atoms. Such alkyl groups preferably are unsubstituted alkyl of up to 4 carbon atoms. When the reactant is an olefin having the formula

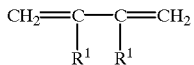   (I)

the $R^1$ substituents may be the same or different. The aryl groups represented by $R^2$ may be unsubstituted or substituted carbocyclic aryl having 6 to 10 carbon atoms, e.g., unsubstituted and substituted phenyl and naphthyl radicals. Examples of the substituents which may be present on the aryl groups include alkyl of up to 4 carbon atoms, alkoxy of up to 4 carbon atoms, halogen such as chloro and bromo, hydroxy, vinyl, and the like.

The epoxides produced from the olefins of formula (I) in accordance with the epoxidation process described herein have the general formula

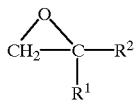   (II)

wherein $R^1$ and $R^2$ are defined above. The process provided by our invention is especially useful for the selective monoepoxidation of butadiene to 3,4-epoxy-1-butene.

The selective epoxidation process provided by this invention is carried out by contacting a gaseous mixture of norbornene, norbornadiene, or an olefin of formula (I) and an oxygen-containing gas with a supported, fluorine-promoted, silver catalyst at a temperature of 125 to 275° C., preferably 170 to 250° C., and a pressure of 1 to 100 bar (100 to 10,000 kPa) absolute, preferably 1–50 bars. Temperatures of 180 to 250° C. and pressures of 1 to 10 bar (100 to 1000 kPa) absolute constitute the preferred operating conditions. The oxygen-containing gas employed may be air, oxygen-enriched air, essentially pure oxygen or oxygen diluted with an inert gas such as helium, argon, nitrogen, etc. The volume ratio of oxygen ($O_2$) to olefin typically is in the range of 10:1 to 1:10. To avoid the existence of explosive mixtures of oxygen and olefin and to provide for better heat transfer and kinetic control, an inert gas may be included in the gaseous feed mixture, e.g., inert gas:oxygen volume ratios in the range of 1:1 to 10:1.

Reaction times suitable for the practice of the present invention may vary within wide ranges. Generally, the contact time is that sufficient to obtain olefin conversion per pass in the range of about 0.1 up to 75 mole percent. The actual contact times required to accomplish the desired conversion levels may vary within wide ranges, depending on such factors as vessel size, olefin to oxygen ratios, the silver loading level on the catalyst, the presence or absence of any catalyst modifiers, the amount of organic halide present in the reaction zone, and the reaction temperature and pressure.

REFERENCE EXAMPLES 1–7

A series of CsF-promoted Ag catalysts were prepared by impregnation of support with a solution of silver compound and promoter in 0.5–3.0 volumes of solvent relative to the volume of support being treated.

In Reference Example 1, 25.0 grams (g) of alumina rings (Norton SA 5552 described hereinabove) were added to a 7.0 g solution of silver nitrate in 50 ml of distilled water in a 250 ml pear-shaped fluted flask. Next 0.6 ml of a CsF promoter solution (10 mg CsF/1.0 ml of distilled water solution) was added to the flask which was placed on a rotary evaporator at 50° C. and tumbled at 20–30 revolutions per minute at atmospheric pressure to wet the alumina rings. The temperature of the flask was increased to 60° C. and the pressure was reduced. When the water began to boil at reduced pressure, the vacuum was released several times to ensure complete wetting within the pores of the alumina support. The water was then removed at about 60° C. and about 0.01 to 500 torr over a period of from 0.5 to 1.0 hours.

When the rate of water collection in the rotary evaporator slowed to about 1 drop every 10 seconds, the impregnated support was transferred to a drier which was placed in a forced air oven preheated to 170° C. and the impregnated support was tumble dried in a stainless steel basket for 30 minutes. A portion of material that adhered to the walls of the flask after drying was discarded. The resulting catalyst precursor could be stored or calcined immediately.

The catalyst precursor was calcined in a single pass flow reactor fabricated from Pyrex (trademark) glass tubing which is 12 inches (30.48 cm) in length with an inside diameter of 0.75 inch (1.91 cm). The catalyst precursor is maintained in place by means of a Pyrex glass frit or Pyrex glass wool. The vessel is positioned in a vertical, programmable, tube furnace and connected to a gas manifold/mass flow controller system which supplies gases to the vessel at a rate of 100 standard cubic centimeters per minute (a gas hourly space velocity of 200 to 2000 depending on the amount of catalyst precursor in the vessel). A stainless steel-clad thermocouple is inserted in the precursor bed through the top of the vessel. The catalyst precursor is heated to 300° C. at a rate of 2 to 10° C. per minute and held at 300° C. for 1 hour while passing a helium-oxygen mixture consisting of 20 volume percent oxygen through the catalyst precursor. The catalyst precursor then is cooled to room temperature over a period of 30 minutes.

The calcined catalyst is reduced by changing the gas supplied by the flow controller system to a reduction gas consisting of 80 volume percent helium and 20 volume percent hydrogen. The reduction gas is passed through the catalyst bed at the rate of 100 standard cubic centimeters per minute while the furnace is heated. The reduction is monitored by the appearance and disappearance of a temperature exotherm. The furnace controller is set so that the temperature exotherm will not exceed 400° C. After the reduction is complete, the active catalyst is subjected to a thermal treatment whereby the temperature of the furnace is increased to and held at 350° C. for 1 hour before cooling to room temperature.

The catalyst obtained (Catalyst I) was analyzed to contain 12.6 weight percent (wt %) silver and 175 ppm by weight Cs based on weight of the finished catalyst. The Ag:Cs weight ratio was 720:1.

Table I below summarizes the results of Reference Example 1–6 in which catalysts made were prepared according to the above method. The amounts of silver nitrate (7.0 g), distilled water (50 ml) and alumina rings (25 g) are the same for each reference example. As indicated below the amount of promoter solution changes. Catalyst VII, described as Reference Example 7, is a catalyst that is unpromoted with either Cs or halide ions.

TABLE I

| Ref. Ex. | Catalyst | Promoter | Promoter Solution (ml) | Ag (wt %) | Cs (ppm) | Ag:Cs Wt. Ratio |
|---|---|---|---|---|---|---|
| 1 | I | F | 0.6 | 12.6 | 175 | 720:1 |
| 2 | II | F | 1.1 | 12.8 | 291 | 440:1 |
| 3 | III | F | 2.3 | 12.5 | 620 | 202:1 |
| 4 | IV | F | 3.4 | 12.3 | 905 | 136:1 |
| 5 | V | F | 5.7 | 12.2 | 1492 | 82:1 |
| 6 | VI | F | 8.0 | 13 | 2126 | 61:1 |
| 7 | VII | None | 0 | 12 | 0 | — |
| 8 | VIII | Cl | — | 12 | 990 | 121:1 |
| 9 | IX | Cl | — | 15.5 | 567 | 273:1 |

REFERENCE EXAMPLE 8

This example, Catalyst VIII, is the same as Catalyst LL in U.S. Pat. No. 4,950,773 and is a silver catalyst promoted with a combination of $CsCl/CsNO_3$ in a 7/1 ratio. Catalyst VIII contained 12.0 wt % Ag and 990 ppm Cs with an Ag:Cs weight ratio of 121:1.

The data from Table III-A below were reported directly from Table 8A of the '773 patent. These data show that with He as the inert diluent the Catalyst VIII became inoperable after being on line for 420 minutes with no organic halide co-feed used.

REFERENCE EXAMPLE 9

The procedure of Reference Example 1 was repeated substantially as described using 140 g of silver nitrate 437.5 mg of CsCl dry powder and 500 g of alumina rings (Norton SA 5552) in 300 ml of distilled water. The silver nitrate and the CsCl were dissolved in the distilled water before the alumina rings were added to the 3000 ml flask. Catalyst IX contained 15.5 wt % Ag and 567 ppm Cs with a Ag:Cs weight ratio of 273:1.

The silver loadings reported in the Reference Examples were determined by inductively coupled plasma atomic emission spectroscopy (ICP-AES). With regard to Reference Examples 1–6, even though comparable amounts of silver compound and support material were employed, differences in analyzed weight percent of silver may be due to varying amounts of material adhering on the walls of the flask.

The Cs loadings reported were determined by flame atomic emission spectroscopy (FAES). Upon drying, calcination and reduction, some of the fluorine may become associated with the Ag, some with the Cs and some with the alumina support. Thus, the analyzed Cs levels in the catalysts do not necessarily represent the amount of fluorine which is active in the catalysts but the relative amount of fluorine in each. As the analyzed Cs level increases so does the amount of fluorine present in the catalyst.

Process Description

In the selective epoxidation process of the following Examples 1–10 and Comparative Examples 1–3 butadiene as the olefin and the various catalysts described above were used. The results reported were obtained while operating at steady state conditions using a pressure of 1 bar (100 kPa) absolute in a single-pass, flow reactor. The reactor tube was fabricated from Pyrex glass tubing and was 12 inches (30.48 cm) in length with an inside diameter of 0.75 inches (1.91 cm). The catalyst charge (8–8.5 g) was held in place in the middle portion of the reactor tube by means of a Pyrex glass frit or glass wool. A Chromel/Alumel alloy thermocouple sheathed in stainless steel was embedded within the catalyst bed to measure reaction temperature. The reactor was heated by means of a tube furnace equipped with a proportional band controller.

The helium diluent and butadiene and oxygen were fed to the reactor in a helium:butadiene:oxygen volume ratio of 4:1:1 at a predetermined gas hourly space velocity using mass flow controllers, which permitted highly accurate and reproducible flow rates of helium, butadiene and oxygen regardless of pressure changes from the supply cylinders or the reactor system downstream from the controllers. The butadiene oxidations were carried out at 225° C. unless stated otherwise.

Analyses of the reaction products and feed compositions were performed using an in-line gas sampling loop connected directly to the inlet of a Varian 3760 gas chromatograph. Both thermal conductivity (TC) and flame ionization (FI) detectors [connected in series below the packed Chromosorb 101 column (8 ft. (2.44 meters) by 2 mm id Pyrex glass capillary column)] were used to analyze all of the reaction products. The TC detector gave quantitative analyses for oxygen, carbon dioxide, water, butadiene, formaldehyde (if present), and butadiene monoxide, while the FI detector was used for trace amounts of organic molecules such as crotonaldehyde, 2,5-dihydrofuran, furan and acrolein. In practice, however, usually only the selective epoxidation product and olefin feedstock were present as organic molecules. Further, by means of a switching valve, it was possible to divert the feed stream through the in-line sample loop prior to passage over the catalyst. In this way, quantitative analysis of the feed stream and comparison to the corresponding data from the reactor effluent were possible, thereby providing very accurate measurements of both conversion levels and product selectivities. Output from both the TC and FI detectors were integrated using computing integrators which were programmed to give both absolute quantities and rates of formation. All reactor exit lines were heated and maintained at 125–140° C. to prevent product condensation.

The GC analysis was performed using the following temperature programming schedule: an initial temperature of 100° C. was held for 5 minutes, followed by a temperature program rate of +10° C./minute up to a final temperature of 200° which was then held for 7 minutes. The helium GC carrier rate was 20 mL/min.

EXAMPLES 1–6 AND COMPARATIVE EXAMPLE 1

Butadiene was epoxidized according to the above-described procedure using Catalysts I-VII at 225° C. The results obtained are shown in Table II wherein CONV is the mole percent conversion of butadiene defined as:

$$\frac{\text{Moles butadiene converted to products}}{\text{Moles butadiene fed}} \times 100$$

and SELECT is the percent selectivity to 3,4-epoxy-1-butene defined as:

$$\frac{\text{Moles butadiene converted to, 3, 4-epoxy-1-butene}}{\text{Moles butadiene converted to total products}} \times 100$$

TABLE II

CATALYSTS I to VII
CATALYSTS: I to VII
FEED: He/Butadiene/Oxygen = 4/1/1
GHSV = 2300 hr$^{-1}$

| EXAMPLE | CATALYST | CONV | SELECT |
|---|---|---|---|
| 1 | I | 2.0 | 84.0 |
| 2 | II | 3.9 | 80.0 |
| 3 | III | 9.4 | 92.4 |
| 4 | IV | 10.3 | 92.0 |
| 5 | V | 10.2 | 91.6 |
| 6 | VI | 1.9 | 95.3 |
| C-1 | VII | 0.8 | 81.0 |

The results reported in Table II demonstrate that the presence of CsF on the catalyst increased both overall conversion of the olefin and conversion of the olefin to the desired epoxide product, i.e., selectivity.

COMPARATIVE EXAMPLE 2 AND EXAMPLE 7

The reaction was run for an extended time period with no organic halide co-feed. Table III-A contains the results for Catalyst VIII at a target temperature of 228° C. and Table III-B the results for Catalyst V at a target temperature of 226° C.

TABLE III-A

COMPARATIVE EXAMPLE 2
CATALYST VIII (Cl promoted)
HELIUM AS DILUENT WITH NO ORGANIC HALIDE CO-FEED
FROM U.S. PAT. NO. 4,950,773 (Table 8A)
CATALYST: LL 990 ppm Cs/12% Ag/A1203 Rings
FEED: He/Butadiene/Oxygen = 4/1/1
GHSV = 2200 hr$^{-1}$

| TIME ON STREAM (MINUTES) | TEMP. (°C.) | % CONVERSION BUTADIENE | % CONVERSION OXYGEN | % SELECTIVITY BUTADIENE MONOXIDE |
|---|---|---|---|---|
| 51 | 228 | 6.4 | 5.1 | 96.6 |
| 76 | 228 | 9.0 | 5.7 | 97.8 |
| 101 | 228 | 11.0 | 7.1 | 97.5 |
| 126 | 228 | 11.6 | 7.5 | 97.6 |
| 154 | 228 | 12.7 | 8.4 | 97.3 |
| 187 | 228 | 13.3 | 8.9 | 97.1 |
| 211 | 228 | 13.4 | 8.9 | 97.2 |
| 240 | 228 | 13.7 | 9.3 | 96.8 |
| 262 | 230 | 14.1 | 9.4 | 97.1 |
| 284 | 231 | 14.4 | 9.6 | 97.1 |
| 307 | 233 | 15.3 | 10.4 | 96.9 |
| 328 | 236 | 16.5 | 11.6 | 96.4 |

TABLE III-A-continued

COMPARATIVE EXAMPLE 2
CATALYST VIII (Cl promoted)
HELIUM AS DILUENT WITH NO ORGANIC HALIDE CO-FEED
FROM U.S. PAT. NO. 4,950,773 (Table 8A)
CATALYST: LL 990 ppm Cs/12% Ag/A1203 Rings
FEED: He/Butadiene/Oxygen = 4/1/1
GHSV = 2200 hr$^{-1}$

| TIME ON STREAM (MINUTES) | TEMP. (°C.) | % CONVERSION BUTADIENE | % CONVERSION OXYGEN | % SELECTIVITY BUTADIENE MONOXIDE |
|---|---|---|---|---|
| 349 | 239 | 17.1 | 12.2 | 96.2 |
| 375 | 243 | 18.5 | 14.5 | 94.7 |
| 401 | 256 | 21.5 | 22.7 | 89.3 |
| 420 | 313 | 16.8 | 60.8 | 39.8 |
| 441 | 402 | 12.1 | 92.0 | 6.7 |
| 460 | 422 | 11.2 | 92.1 | 1.4 |

TABLE III-B

EXAMPLE 7
CATALYST V (F promoted)
HELIUM AS DILUENT WITH NO ORGANIC HALIDE CO-FEED
CATALYST: 1492 ppm Cs/12.2% Ag/A1203 Rings
FEED: He/Butadiene/Oxygen = 4/1/1
GHSV = 2300 hr$^{-1}$

| TIME ON STREAM (MINUTES) | TEMP. (°C.) | % CONVERSION BUTADIENE | % CONVERSION OXYGEN | % SELECTIVITY BUTADIENE MONOXIDE |
|---|---|---|---|---|
| 56 | 200 | 4.5 | 5.6 | 94.6 |
| 72 | 205 | 5.5 | 6.2 | 93.7 |
| 96 | 211 | 6.9 | 6.5 | 94.5 |
| 114 | 216 | 8.1 | 7.4 | 92.9 |
| 145 | 220 | 9.1 | 7.4 | 93.2 |
| 166 | 223 | 10.0 | 7.8 | 92.6 |
| 189 | 225 | 10.5 | 8.3 | 92.3 |
| 210 | 226 | 10.5 | 8.6 | 91.7 |
| 300 | 226 | 10.8 | 9.1 | 92.0 |
| 348 | 226 | 10.9 | 8.3 | 91.8 |
| 377 | 226 | 10.8 | 8.3 | 91.9 |
| 414 | 226 | 10.7 | 8.3 | 91.3 |
| 480 | 226 | 10.8 | 8.3 | 91.2 |
| 542 | 226 | 10.6 | 8.4 | 91.5 |
| 565 | 226 | 10.7 | 8.3 | 91.5 |
| 596 | 226 | 10.8 | 8.3 | 91.1 |
| 643 | 226 | 10.8 | 8.4 | 91.6 |
| 670 | 226 | 10.7 | 8.4 | 91.1 |
| 691 | 226 | 10.8 | 8.4 | 91.2 |
| 751 | 226 | 10.8 | 8.6 | 91.7 |
| 787 | 226 | 10.7 | 8.3 | 91.6 |
| 838 | 226 | 10.7 | 8.3 | 91.7 |
| 920 | 226 | 10.9 | 7.8 | 91.7 |
| 1014 | 226 | 10.7 | 7.7 | 91.7 |
| 1146 | 226 | 10.6 | 7.8 | 91.7 |
| 1206 | 226 | 10.9 | 7.8 | 91.5 |
| 1234 | 226 | 10.8 | 7.9 | 91.6 |
| 1276 | 226 | 10.9 | 8.1 | 91.3 |
| 1326 | 226 | 11.0 | 8.3 | 91.0 |
| 1370 | 226 | 10.8 | 8.5 | 90.9 |
| 1400 | 226 | 10.8 | 8.4 | 91.6 |
| 1431 | 226 | 10.8 | 8.4 | 91.2 |
| 1460 | 226 | 10.7 | 8.3 | 91.5 |
| 1498 | 226 | 10.8 | 8.7 | 90.9 |
| 1521 | 226 | 10.8 | 9.0 | 90.9 |
| 1544 | 226 | 10.7 | 8.5 | 91.6 |
| 1565 | 226 | 10.8 | 9.0 | 90.9 |
| 1585 | 226 | 10.7 | 8.9 | 91.4 |

The results reported in Tables III-A and III-B demonstrate the improved operability (resistance to thermal run-away) of the CsF-promoted silver catalyst as compared to the CsCl-promoted silver catalyst of the prior art.

COMPARATIVE EXAMPLE 3 AND EXAMPLE 8

The reaction was run for an extended time period with normal butane as the inert diluent and no organic halide co-feed. Table IV-A contains the results for Catalyst IX at a target temperature of 226° C. and Table IV-B the results for Catalyst V at a target temperature of 2260° C.

TABLE IV-A

COMPARATIVE EXAMPLE 3
CATALYST IX (Cl promoted)
BUTANE AS DILUENT WITH NO ORGANIC HALIDE CO-FEED
CATALYST: 567 ppm Cs/15.5% Ag/A1203 Rings
FEED: He/Butadiene/Oxygen = 4/1/1
GHSV = 2300 hr$^{-1}$

| TIME ON STREAM (MINUTES) | TEMP. (°C.) | % CONVERSION BUTADIENE | OXYGEN | % SELECTIVITY BUTADIENE MONOXIDE |
|---|---|---|---|---|
| 67 | 187 | 7.3 | 9.7 | 93.8 |
| 90 | 192 | 8.9 | 10.0 | 93.6 |
| 125 | 193 | 9.7 | 10.2 | 93.2 |
| 151 | 199 | 12.0 | 10.0 | 92.7 |
| 177 | 204 | 14.4 | 11.3 | 91.3 |
| 239 | 204 | 12.7 | 10.8 | 90.3 |
| 262 | 209 | 15.3 | 12.7 | 87.9 |
| 280 | 211 | 17.1 | 13.0 | 87.0 |
| 308 | 213 | 16.2 | 13.1 | 86.5 |
| 327 | 267 | 14.0 | 50.2 | 35.1 |
| 345 | 382 | 11.1 | 91.6 | 1.8 |

TABLE IV-B

EXAMPLE 8
CATALYST V (F promoted)
BUTANE AS DILUENT WITH NO ORGANIC HALIDE CO-FEED
CATALYST: 1492 ppm CS/12.2% Ag/A1203 Rings
FEED: He/Butadiene/Oxygen = 4/1/1
GHSV = 2300 hr$^{-1}$

| TIME ON STREAM (MINUTES) | TEMP. (°C.) | % CONVERSION BUTADIENE | OXYGEN | % SELECTIVITY BUTADIENE MONOXIDE |
|---|---|---|---|---|
| 76 | 194 | 3.4 | 10.7 | 93.6 |
| 97 | 200 | 4.4 | 11.2 | 93.3 |
| 124 | 205 | 5.5 | 11.1 | 92.9 |
| 167 | 212 | 6.9 | 11.4 | 92.7 |
| 196 | 217 | 8.3 | 12.9 | 91.8 |
| 216 | 219 | 8.9 | 12.9 | 91.5 |
| 311 | 219 | 8.2 | 12.8 | 91.5 |
| 396 | 222 | 8.7 | 12.0 | 90.6 |
| 424 | 222 | 9.0 | 12.6 | 90.7 |
| 501 | 222 | 9.0 | 12.9 | 90.3 |
| 570 | 223 | 9.1 | 12.1 | 90.7 |
| 691 | 221 | 8.8 | 13.0 | 89.2 |
| 784 | 223 | 9.7 | 11.1 | 90.3 |
| 827 | 223 | 9.7 | 11.1 | 90.4 |
| 859 | 223 | 10.0 | 10.8 | 90.4 |
| 935 | 225 | 11.0 | 10.6 | 89.4 |
| 989 | 226 | 10.8 | 10.8 | 89.6 |
| 1055 | 226 | 11.0 | 10.7 | 89.5 |
| 1100 | 226 | 11.0 | 11.1 | 89.5 |
| 1180 | 226 | 10.9 | 10.7 | 89.5 |
| 1297 | 226 | 11.4 | 10.4 | 89.6 |
| 1359 | 226 | 11.1 | 10.4 | 89.6 |
| 1418 | 226 | 11.0 | 10.1 | 90.0 |
| 1494 | 226 | 11.1 | 10.1 | 89.5 |

TABLE IV-B-continued

EXAMPLE 8
CATALYST V (F promoted)
BUTANE AS DILUENT WITH NO ORGANIC HALIDE CO-FEED
CATALYST: 1492 ppm CS/12.2% Ag/A1203 Rings
FEED: He/Butadiene/Oxygen = 4/1/1
GHSV = 2300 hr$^{-1}$

| TIME ON STREAM (MINUTES) | TEMP. (°C.) | % CONVERSION BUTADIENE | OXYGEN | % SELECTIVITY BUTADIENE MONOXIDE |
|---|---|---|---|---|
| 1635 | 226 | 11.0 | 10.2 | 89.6 |
| 1677 | 226 | 10.8 | 10.0 | 89.9 |
| 1794 | 226 | 11.3 | 9.8 | 89.6 |
| 1864 | 226 | 11.0 | 9.8 | 90.2 |
| 1909 | 226 | 11.0 | 9.4 | 89.8 |
| 1934 | 226 | 10.8 | 9.4 | 90.4 |
| 2101 | 226 | 10.8 | 9.4 | 90.1 |
| 2161 | 226 | 10.7 | 10.2 | 90.5 |
| 2205 | 226 | 10.8 | 9.9 | 90.5 |
| 2285 | 226 | 10.7 | 10.3 | 90.4 |
| 2376 | 226 | 10.7 | 10.0 | 90.3 |
| 2501 | 226 | 10.8 | 10.5 | 89.8 |
| 2566 | 226 | 10.7 | 10.5 | 90.2 |
| 2626 | 226 | 10.7 | 10.0 | 90.3 |
| 2686 | 226 | 10.9 | 10.1 | 90.4 |
| 2715 | 226 | 10.7 | 10.8 | 90.1 |

The results in Tables IV-A and IV-B again demonstrate the improved operability of the CsF-promoted catalysts.

EXAMPLES 9 AND 10

The reaction was run with the addition of 1,2-dichloroethane (DCE) as a co-feed to the reactor in ppm levels to serve as a reaction moderator.

TABLE V

ORGANIC HALIDE CO-FEED
CATALYST: III
FEED: He/Butadiene/Oxygen = 4/1/1
GHSV = 2300 hr$^{-1}$

| EXAMPLE | DCE | CONV | SELECT |
|---|---|---|---|
| 3 | 0 | 9.4 | 92.4 |
| 9 | 5 | 9.2 | 92.6 |
| 10 | 10 | 8.9 | 93.6 |

Since the fluorine is eventually depleted from the catalysts surface (though at a much slower rate compared to other halides), an organic halide reaction moderator gas is preferably utilized to operate the catalyst on a time scale that is desirable industrially. Examples 9 and 10 and Table V demonstrated that with an organic chloride co-feed such as 1,2-dichloroethane the reaction could be run for longer periods of time. Optionally, as described in U.S. Pat. No. 5,155,242 the chlorohydrocarbons may be substituted with fluorohydrocarbons.

The CsF-promoted Ag catalyst supported on $Al_2O_3$ exhibits greater operability (resistance to run-away) under standard reaction conditions making control of the process easier and reduces the risks involved in operations due to rapid lose of selectivity with accompanying thermal run-aways, catalyst degradation and lose of valuable butadiene feed stock. This is an especially important benefit during start-up of the butadiene epoxidation process, when non-steady state reaction conditions are encountered. The improved operability of the CsF promoted catalyst greatly improves the ease of reaction start-up.

The invention has been described in detail with particular reference to preferred processes thereof, but it will be understood that variations and modifications can be effected within the spirit and scope of the invention.

We claim:

1. Process for the preparation of a monoepoxide of an olefin selected from norbornene, norbornadiene and olefins having the general formula

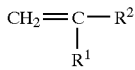   (I)

wherein $R^1$ is hydrogen or alkyl and $R^2$ is an aryl group, a tertiary alkyl group of the group having the formula

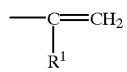

with the proviso that $R^1$ contains no hydrogen atoms in a position allylic to the ethylenic unsaturation, which comprises contacting the olefin with an oxygen-containing gas in the presence of a supported, fluorine-promoted, silver catalyst at epoxide-forming conditions or pressure and temperature, wherein the catalyst consists essentially of a catalyst support material having a surface area of less than 10 square meters per gram having distributed on the surface thereof 0.1 to 50 weight percent silver and cesium fluoride in an amount which provides 10 to 5000 ppm fluorine.

2. Process according to claim 1 wherein the catalyst consists essentially of an alumina catalyst support material having a surface are of less than 2 square meters per gram having distributed on the surface thereof 2 to 25 weight percent silver and cesium fluoride in an amount which provides 20 to 3000 ppm fluorine in a silver:fluorine weight ratio of 100:1 to 2500:1.

3. Process for the preparation of a monoepoxide of an olefin selected from norbornene, norbornadiene and olefins having the general formula

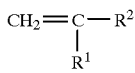   (I)

wherein $R^1$ is hydrogen or alkyl and $R^2$ is an aryl group, a tertiary alkyl group of the group having the formula

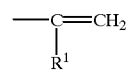

with the proviso that $R^1$ contains no hydrogen atoms in a position allylic to the ethylenic unsaturation, which comprises contacting the olefin with an oxygen-containing gas in the presence of a supported, fluorine-promoted, silver catalyst at a temperature of 200 to 250° C., wherein the catalyst consists essentially of an alumina catalyst support material having a surface area of 0.1 to 2 square meters per gram having distributed on the surface thereof 5 to 20 weight percent silver and cesium fluoride in an amount which provides 50 to 2000 ppm fluorine.

4. Process for the preparation of 3,4-epoxy-1-butene which comprises contacting butadiene with an oxygen-containing gas in the presence of a supported, fluorine-promoted, silver catalyst at epoxide-forming conditions of pressure and temperature, wherein the catalyst consists essentially of a catalyst support material having a surface area of less than 10 square meters per gram having distributed on the surface thereof 1 to 30 weight percent silver and cesium fluoride in an amount which provides 10 to 5000 ppm fluorine in a silver:fluorine weight ratio of 50:1 to 4000:1.

5. Process according to claim 4 wherein the catalyst consists essentially of an alumina catalyst support material having a surface area of less than 2 square meters per gram having distributed on the surface thereof 2 to 25 weight percent silver and cesium fluoride in an amount which provides 20 to 3000 ppm fluorine in a silver:fluorine weight ratio of 100:1 to 2500:1.

6. Process for the preparation of 3,4-epoxy-1-butene which comprises contacting butadiene with an oxygen-containing gas in the presence of a supported, fluorine-promoted, silver catalyst at a temperature of 200 to 250° C., wherein the catalyst consists essentially of an alumina catalyst support material having a surface area of 0.1 to 2 square meters per gram having distributed on the surface thereof 5 to 20 weight percent silver and cesium fluoride in an amount which provides 50 to 1600 ppm fluorine in a silver:fluorine weight ratio of 100:1 to 2000:1.

* * * * *

UNITED STATES PATENT AND TRADEMARK OFFICE
CERTIFICATE OF CORRECTION

PATENT NO. : 5,908,942
DATED : June 1, 1999
INVENTOR(S) : George Leslie Oltean, John Robert Monnier It is certified that error appears in the above-identified patent and that said Letters Patent is hereby corrected as shown below:

Column 13, Line 33 (Claim 2, Line 3) "surface are" should be ---surface area---

Signed and Sealed this

Second Day of November, 1999

Attest:

Attesting Officer

Q. TODD DICKINSON

Acting Commissioner of Patents and Trademarks